United States Patent [19]

Ahtiainen

[11] 4,259,632
[45] Mar. 31, 1981

[54] CONTINUOUS ACTION CAPACITIVE MOISTURE MEASURING APPARATUS

[75] Inventor: Ari J. Ahtiainen, Helsinki, Finland

[73] Assignee: OT-tehdas Oy, Finland

[21] Appl. No.: 960,063

[22] Filed: Nov. 13, 1978

[30] Foreign Application Priority Data

Nov. 18, 1977 [FI] Finland .................................. 773492

[51] Int. Cl.³ ............................................ G01R 27/26
[52] U.S. Cl. .............................. 324/61 R; 324/61 QL; 73/73
[58] Field of Search .............. 324/61 R, 61 P, 61 QL; 73/73

[56] References Cited

U.S. PATENT DOCUMENTS

| 3,508,435 | 4/1970 | Ivy ......................................... 73/73 X |
| 3,626,286 | 12/1971 | Rauchwerger .................... 324/61 R |
| 3,641,431 | 2/1972 | Pigage et al. ...................... 324/61 R |
| 3,651,505 | 3/1972 | Schmidt ........................ 324/61 R X |
| 4,013,065 | 3/1977 | Copeland et al. .................... 73/73 X |
| 4,122,708 | 10/1978 | Maier .............................. 324/61 R X |

FOREIGN PATENT DOCUMENTS 1253531  3/1960  France ................................... 324/61 P Primary Examiner—Stanley T. Krawczewicz
Attorney, Agent, or Firm—Steinberg & Raskin

[57] ABSTRACT

Capacitive moisture measuring apparatus for continuously measuring the moisture content of granular material, such as grain, includes a series circuit including a measuring capacitor whose capacitance varies as a function of moisture content of granular material in which it is immersed during operation and a resistor coupled to the measuring capacitor, and an oscillator for generating a voltage signal of stable frequency and amplitude which is applied to the circuit. An operational amplifier is serially coupled to a diode to constitute an ideal diode, the latter being coupled across the measuring capacitor.

5 Claims, 1 Drawing Figure

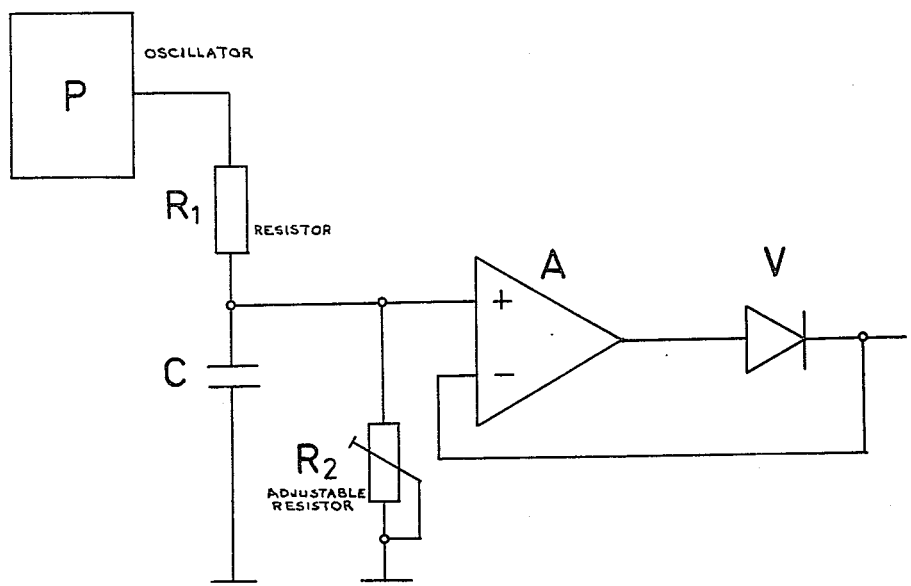

CONTINUOUS ACTION CAPACITIVE MOISTURE MEASURING APPARATUS

BACKGROUND OF THE INVENTION

This invention relates generally to moisture measuring apparatus and, more particularly, to capacitive moisture measuring apparatus for measuring the moisture content of granular material.

Moisture measuring apparatus which utilize capacitors whose capacitance vary as a function of the moisture of the material being measured are known. For example, in the measurement of the moisture of granular material, and, in particular, in measuring the moisture of grain, it is known that the moisture content of the material usually varies in the range of 10 to 40%. However, it is particularly important to obtain the highest possible degree of accuracy in moisture measurement in the moisture range of from about 12 to 17%. The use of a capacitive measuring apparatus when the moisture level falls within this range has proven to be especially advantageous since the dielectric constant of such material varies in a substantially linear manner within a moisture range of from about 4 to 18%. Since the dielectric constant varies in an abrupt manner as the moisture content exceeds 18%, measuring apparatus utilizing variations in resistance obtain greater accuracy than capicitance methods and apparatus in that range.

Moisture measuring apparatus utilizing the moisture dependent variations in the capacitance of a capacitor are disclosed in U.S. Pat. Nos. 3,508,435 and 3,626,286. More particularly, the measuring apparatus disclosed in U.S. Pat. No. 3,508,435 utilizes a series circuit comprising a resonance circuit and a resistor, the series circuit being driven by an oscillator supplying a voltage at a frequency of 15 kHz. The moisture measuring apparatus disclosed in U.S. Pat. No. 3,626,286, utilizes an oscillator which supplies a peak to peak voltage of 100 volts at a frequency of 75 kHz to a measuring circuit comprising two capacitors, one of the capacitors functioning as a measuring capacitor while the other capacitor having a known capacitance. In this latter apparatus the detector input voltage is derived from the voltage division effected by the pair of capacitors.

Conventional capacitive moisture measuring apparatus of the type described above have proven to be not entirely satisfactory. Thus, such prior art apparatus are extremely complex in construction and, accordingly expensive in manufacture. Accordingly, such prior art capacitive moisture measuring apparatus are not particularly suited for manufacture in mass production. Further, by virtue of their relatively complicated design, such prior art measuring apparatus are not as reliable as is desired.

SUMMARY OF THE INVENTION

Accordingly, one object of the present invention is to provide a new and improved continuous action capacitive moisture measuring apparatus.

Another object of the present invention is to provide such a continuous action capacitive moisture measuring apparatus which is relatively simple in design, reliable in operation and which is amenable to mass production.

Briefly, in accordance with the present invention, these and other objects are obtained by providing a series circuit including a measuring capacitor having a capacitance which varies as a function of moisture content of the material being measured and a resistor coupled in series therewith. An oscillator supplies a voltage of predetermined frequency and amplitude to the series circuit. An operational amplifier coupled in series with a diode thereby forming an ideal diode is coupled across the measuring capacitor, the latter of which is immersed in the granular material whose moisture is to be measured.

DESCRIPTION OF THE DRAWING

A more complete appreciation of the invention and many of the attendant advantages thereof will be readily appreciated as the same becomes better understood by reference to the following detailed description when considered in connection with the accompanying drawing which comprises a schematic illustration of the circuitry of the measuring apparatus of the present invention.

DESCRIPTION OF THE PREFERRED EMBODIMENT

Referring now to the drawing, the moisture measuring apparatus of the present invention generally comprises an oscillator P which generates a predetermined voltage having a substantially stable frequency and amplitude, which voltage is supplied to a series circuit comprising a measuring capacitor C and a resistor $R_1$. An operational amplifier A coupled to a diode V as shown in the Figure in a manner so as to constitute a so-called ideal diode, is coupled across the measuring capacitor C. Further, an adjustable variable resistor $R_2$ is also coupled across the measuring capacitor C for purposes of calibration, discussed in greater detail below.

The oscillator P impresses an alternating voltage on the measuring circuit having a constant wave form which is relatively stable in frequency and amplitude. However, it should be noted that such an oscillator need not necessarily employ a crystal in the generation of the voltage.

The peak to peak amplitude of the AC voltage is preferably within the range of between 5 and 20 volts. The range of frequency of the voltage supplied by the oscillator is between 1 and 250 kHz. This range is required since 1 kHz is about the lowest frequency at which charging of the capacitor will be effective in the case of grain material having high moisture content. Thus, the frequency of the oscillator is preferably not less then 1 kHz. The upper value of the frequency range is about 250 kHz since the functioning of the operational amplifier A which obtains the measuring signal output is not satisfactory at frequencies higher then this value due to the relatively simple design of the circuit of the present invention. The variable resistor $R_2$ is adjusted in order to compensate for mechanical variations which may exist in the measuring capacitor C.

In operation, the measuring capacitor C of the measuring circuit comprising capacitor C and resistor $R_1$ is immersed in the mass of granular material. The value of the resistance of resistor $R_1$ is predetermined so as to achieve maximum sensitivity of the measuring capacitor in a particular desired moisture range. Thus, for example, for a particular granular material, maximum sensitivity of the measuring circuit will be obtained for a moisture content of 14% and, in this case, the resistance of resistor $R_1$ is chosen to be equal to the capacitive reactance of the measuring capacitor C. During operation, the operational amplifier A which is serially connected to the diode V to constitute an ideal diode, serves to eliminate the effect of the threshold voltage so as to improve the sensitivity and thermal stability of the measuring circuit. The ideal diode is electrically connected at the common terminal of resistor $R_1$ and measuring capacitor C to rectify the voltage appearing at that common terminal and which voltage is indicative of the moisture content of the granular material being measured. Thus, the rectified voltage may be supplied to a measuring instrument (not shown) connected to the output of the ideal diode for indicating the moisture content of the granular material.

Tests have been conducted utilizing the circuitry of the present invention to measure the moisture of granular material. It has been found that the highest accuracy is obtained in the moisture range of about 12 to 17 percent. In this range, the present invention achieves an accuracy of plus or minus 0.5 to 1 percent. Such tolerance in measurements in this range are entirely satisfactory.

Since a variation in the temperature of a granular material having a constant moisture content will result in a variation in the capacitance of the measuring capacitor, it is recognized that to some extent, the capacitance of capacitor C is temperature dependent. Such temperature dependance, however, may be compensated as will be readily understood by those skilled in the art in a manner such that the accuracy of the measuring apparatus may be still further improved. Further improvement in the accuracy of the measurements obtained by the present invention may be obtained by various additional expedients which are readily apparent to those skilled in the art.

Obviously, numerous modifications and variations of the present invention are possible on the light of the above teachings. Accordingly, it is understood that the invention may be practiced otherwise then as specifically disclosed herein.

What is claimed is:

1. Apparatus for measuring the moisture of granular material comprising:
    a series circuit including a measuring capacitor having a capacitance which varies as a function of moisture content, and a resistor coupled in series with said measuring capacitor;
    oscillator means for generating a voltage of substantially stable frequency and amplitude, said voltage being applied to said circuit;
    an operational amplifier serially coupled to a diode to constitute an ideal diode, the latter being coupled across said measuring capacitor; and
    an adjustable resistor coupled across said measuring capacitor whereby the resistance of said adjustable resistor is adjustable to calibrate the capacitance of said capacitor.

2. Apparatus as recited in claim 1 wherein the frequency of the oscillator means is in the range of between 1 and 250 kHz.

3. Apparatus as recited in claim 2 wherein the frequency of the oscillator means is about 100 kHz.

4. Apparatus as recited in claim 1 wherein the capacitance of said capacitor is about 10 pF.

5. Apparatus as recited in claim 1 wherein the resistance of said resistor is about 150 k $\Omega$.

* * * * *